(12) United States Patent
Jacobsen

(10) Patent No.: US 11,413,241 B2
(45) Date of Patent: Aug. 16, 2022

(54) METHOD FOR PREPARING A COMPOSITION WITH A LOW DISSOLVED OXYGEN CONTENT, COMPRISING ACETAMINOPHEN, AND OPTIONALLY ONE OR MORE NSAIDS, AND A COMPOSITION OBTAINED THEREOF

(71) Applicant: Hyloris Developments SA, Liège (BE)

(72) Inventor: Thomas Jacobsen, Liège (BE)

(73) Assignee: Hyloris Developments SA, Liège (BE)

( * ) Notice: Subject to any disclaimer, the term of this patent is extended or adjusted under 35 U.S.C. 154(b) by 284 days.

(21) Appl. No.: 16/605,711

(22) PCT Filed: Apr. 20, 2018

(86) PCT No.: PCT/EP2018/060205
§ 371 (c)(1),
(2) Date: Oct. 16, 2019

(87) PCT Pub. No.: WO2018/193099
PCT Pub. Date: Oct. 25, 2018

(65) Prior Publication Data
US 2021/0338578 A1    Nov. 4, 2021

(30) Foreign Application Priority Data
Apr. 20, 2017   (WO) .................. PCT/EP2017/059440

(51) Int. Cl.
| A61K 9/08 | (2006.01) |
| A61K 9/00 | (2006.01) |
| A61K 31/167 | (2006.01) |
| A61K 31/192 | (2006.01) |
| A61K 47/02 | (2006.01) |
| A61K 47/10 | (2017.01) |
| A61K 47/20 | (2006.01) |
| A61K 47/26 | (2006.01) |

(52) U.S. Cl.
CPC .............. *A61K 9/08* (2013.01); *A61K 9/0019* (2013.01); *A61K 31/167* (2013.01); *A61K 31/192* (2013.01); *A61K 47/02* (2013.01); *A61K 47/10* (2013.01); *A61K 47/20* (2013.01); *A61K 47/26* (2013.01)

(58) Field of Classification Search
CPC ........ A61K 47/26; A61K 47/20; A61K 47/10; A61K 47/02; A61K 31/192; A61K 31/167; A61K 9/0019; A61K 9/08
See application file for complete search history.

(56) References Cited

U.S. PATENT DOCUMENTS

| 6,028,222 | A | 2/2000 | Dietlin et al. |
| 6,992,218 | B2 | 1/2006 | Dietlin et al. |
| 11,213,498 | B2 | 1/2022 | Jacobsen |
| 11,219,609 | B2 | 1/2022 | Jacobsen |
| 2004/0054012 | A1 | 3/2004 | Dietlin |
| 2006/0100578 | A1 | 5/2006 | Lieberman |
| 2011/0039939 | A1 | 2/2011 | Al Dandachi Atassi |
| 2012/0035267 | A1 | 2/2012 | Dasberg et al. |
| 2013/0210922 | A1 | 8/2013 | Tseti et al. |
| 2013/0225685 | A1 | 8/2013 | Atkinson |
| 2013/0245591 | A1 | 9/2013 | Pavliv et al. |
| 2017/0209398 | A1 | 7/2017 | Jacobson |
| 2019/0343785 | A1 | 11/2019 | Jacobson |

FOREIGN PATENT DOCUMENTS

| BE | 1020614 | 1/2014 |
| CN | 103298464 | 9/2013 |
| EP | 2620124 | 7/2013 |
| JP | 2011-508768 | 3/2011 |
| JP | 2012-505830 | 3/2012 |
| JP | 2012-524738 | 10/2012 |
| JP | 2013-541583 | 11/2013 |
| WO | WO 2009/083759 | 7/2009 |
| WO | WO 2010/044681 | 4/2010 |
| WO | WO 2010/121762 | 10/2010 |
| WO | WO 2011/018522 | 2/2011 |
| WO | WO 2012/060719 | 5/2012 |
| WO | WO 2013/108180 A1 | 7/2013 |
| WO | WO 2013/138628 | 9/2013 |
| WO | WO 2016/008546 A1 | 1/2016 |

OTHER PUBLICATIONS

International Search Report issued in application No. PCT/EP2018/060205, dated May 25, 2018.
International Search Report issued in application No. PCT/EP2017/059440, dated Dec. 8, 2017.
International Preliminary Report on Patentability issued in application No. PCT/EP2018/060205, dated Aug. 2, 2019.
Fairbrother, "Acetaminophen," Analytical Profiles of Drug Substances, 1974, 3, 1-109.
Koshy et al., "Stability of aqueous solutions of N-acetyl-p-aminophenol," Journal of Pharmaceutical Sciences, Feb. 1. 1961, 50(2):113-8.

(Continued)

*Primary Examiner* — Genevieve S Alley
(74) *Attorney, Agent, or Firm* — Fish & Richardson P.C.

(57) ABSTRACT

The present invention provides a method for preparing an intravenously administrable aqueous composition comprising acetaminophen, and optionally one or more non-steroidal anti-inflammatory drugs (NSAIDs), whereby the dissolved oxygen of the composition in a closed container is maximally 1.0 ppm, said method comprises rinsing at least once a compounding vessel with water of a temperature of at least 80° C., thereby heating the vessel and creating an oxygen low environment in said vessel; and in said rinsed vessel dissolving acetaminophen in water for injection, said water for injection is at a temperature of at least 80° C., whereby optionally one or more NSAIDS are added prior or after dissolving of acetaminophen.

18 Claims, No Drawings

(56) References Cited

OTHER PUBLICATIONS

Shaw et al., "The Effect of Selected Water-Soluble Excipients on the Dissolution of Paracetamol and Ibuprofen," Drug Development and Industrial Pharmacy, vol. 31(6), pp. 515-525 (Jul. 1, 2005).
Yasmeen et al., "Dissolution Method Development and Validation for Combination of Ibuprofen and Paracetamol Tablets," Asian Journal of Pharmaceutical and Clinical Research. vol. 6, Suppl 2, 2013.

METHOD FOR PREPARING A COMPOSITION WITH A LOW DISSOLVED OXYGEN CONTENT, COMPRISING ACETAMINOPHEN, AND OPTIONALLY ONE OR MORE NSAIDS, AND A COMPOSITION OBTAINED THEREOF

This application is the U.S. National Phase under 35 U.S.C. § 371 of International Application PCT/EP2018/060205, filed Apr. 20, 2018, designating the U.S., and published in English as WO 2018/193099 on Oct. 25, 2018, which claims priority to PCT/EP2017/059440, filed Apr. 20, 2017, the entire contents of which are incorporated herein by reference.

TECHNICAL FIELD

The present invention relates to a method for preparing an intravenously administrable aqueous composition comprising acetaminophen, and optionally one or more non-steroidal anti-inflammatory drug, preferably ibuprofen. In a second aspect, the current invention provides for an intravenously administrable aqueous composition comprising acetaminophen, and optionally one or more NSAIDs, preferably ibuprofen.

BACKGROUND

Acetaminophen, also known as paracetamol, is a known non-opiate, non-salicylate analgesic and antipyretic drug. Its chemical name is N-(4-hydroxyphenyl)acetamide. It provides temporary relief of minor aches and pains with heartburn or acid ingestion and upset stomach associated with these symptoms.

It is known that acetaminophen is susceptible to oxidation. Its stability in aqueous solutions therefor requires the removal of oxygen from the solution and/or the use of anti-oxidants. Another disadvantage is that oxidation products lead to the formation of coloured compounds, making the aqueous solution unsuitable for therapeutic applications.

The current state of the art comprises several methods for removing oxygen from an aqueous solution comprising acetaminophen: U.S. Pat. No. 6,992,218 discloses a method for preparing an aqueous solution comprising acetaminophen and a dissolved oxygen content of less than 2 ppm. The method disclosed in U.S. Pat. No. 6,992,218 comprises deoxygenation of the aqueous solution by bubbling with at least one inert gas and/or inducing vacuum, until the oxygen content is below 2 ppm. U.S. Pat. No. 6,028,222 is directed to a stable, liquid formulation consisting essentially of acetaminophen dispersed in an aqueous medium containing a buffering agent and at least one member of the group consisting of a free radical scavenger and a radical antagonist, wherein the aqueous medium has been deoxygenated by bubbling a water-insoluble inert gas. In turn, WO 2016 008 546 discloses a process for manufacturing an aqueous composition comprising ibuprofen and paracetamol in combination having a dissolved oxygen content of below 2 ppm. This oxygen content is obtained by using an aqueous solvent having a temperature between 85° C. and 99° C., bubbling by an inert gas, and/or applying a vacuum.

However, the methods for removing oxygen from an acetaminophen-comprising aqueous solution described in the current state of the art all comprise a deoxygenation step of the aqueous solution. Deoxygenation steps are known to be relatively complex, energy-demanding and time-consuming.

Furthermore, it is known that acetaminophen in aqueous solution is also liable to undergo hydrolysis thereby forming p-aminophenol There remains a demand for an improved preparation method of stable composition comprising a low dissolved oxygen content.

It is the object of the current invention to provide an easy and straightforward methodology for manufacturing a stable acetaminophen solution suitable for intravenous use. Preferably, this methodology does not require deoxygenation of the formulation once prepared, resulting in a cost-effective and straightforward production process.

It is furthermore the object of the current invention to provide a combination product comprising acetaminophen and one or more NSAIDs, such a ibuprofen.

Combinations of paracetamol and ibuprofen for intravenous administration are known. U.S. Pat. No. 2,013,022 568 5 for instance describes a composition which comprises a specific dose of acetaminophen and ibuprofen for providing pain relief and relief in inflammation. The combination of both active ingredients was found to provide a beneficial effect when administered to patients.

Ibuprofen is very poorly soluble in water and tends to precipitate. As a consequence dosage forms such as oral or injectable compositions have been difficult to develop. An approach followed to improve water solubility has been the use of water-soluble complexes and the preparation of an ibuprofen salt such as sodium or with an amino acid.

There remains however still a need in the art to provide a stable solution of ibuprofen, useful for intravenous use. Preferably, such solution is a combination of acetaminophen and ibuprofen, whereby both active ingredients remain in solution and remain stable over time It is therefore also the aim of the present invention to provide a method for preparing an intravenously administrable aqueous composition of acetaminophen, and ibuprofen, which results in a stable intravenously administrable aqueous composition.

SUMMARY OF THE INVENTION

The present invention provides a solution for at least one of the problems mentioned above, by providing a method for preparing an intravenously administrable aqueous composition comprising acetaminophen, and optionally one or more NSAIDs, preferably ibuprofen, without needing to perform a deoxygenation of the composition.

In a first aspect, the present invention provides a new method for preparing an intravenously administrable aqueous composition according to claim 1.

In particular, the present invention provides in a method for preparing an intravenously administrable aqueous composition comprising acetaminophen, and optionally one or more non-steroidal anti-inflammatory drugs (NSAIDs), whereby the dissolved oxygen of the final composition when in a closed container is maximally 1.0 ppm, and whereby the method comprises the steps of rinsing a compounding vessel with water, preferably water for injection of a temperature of at least 80° C., more preferably at least 90° C. or between 80 and 99° C., thereby heating the vessel and creating an oxygen low environment in said vessel; and dissolving acetaminophen in water for injection, said water for injection is at a temperature of at least 80° C. more preferably at least 90° C. or between 80 and 99° C. The water for injection may optionally, at the time of addition of the acetaminophen, comprise one or more excipients. In a further embodiment, one or more NSAIDs such as ibuprofen is added to the composition. The addition of the NSAIDs may occur prior or after addition of acetaminophen to the water for injection.

More specifically, the method of the current invention comprises in a further preferred embodiment the following steps:

rinsing a compounding vessel with water, preferably water for injection of a temperature of at least 80° C., thereby heating the vessel and creating an oxygen low environment in said vessel;

introducing into said compounding vessel one or more excipients, preferably one or more isotonic agents and one or more pH-adjusting agents, and optionally one or more NSAIDs;

adding water for injection at a temperature of 80-99° C., and mixing said introduced excipients and water;

subsequently dissolving acetaminophen into said mixture; and adding one or more anti-oxidants, and optionally one or more pH adjusting agents to the mixture, thereby obtaining said composition; whereby subsequent to the introduction of a constituent of said composition to said vessel, said vessel is put under nitrogen pressure.

A method according to the present invention has the advantage that no deoxygenation of the composition needs to occur in order to prevent the degradation of acetaminophen. Due to the fact that the vessel in which the composition is prepared is rinsed several times with hot water, the oxygen level in the vessel is reduced. This is achieved by the evacuation of air and thus oxygen from the vessel, by the steam which occurs during rinsing. By using heated water for the preparation of the formulation, the oxygen level will remain low. By providing a nitrogen pressure in the vessel each time the tank is opened for the introduction of constituents, re-oxygenation of the formulation above un unacceptable level is prevented.

In a second aspect, the present invention provides in a stable intravenously administrable aqueous composition. More in particular, the present invention provides an intravenously administrable aqueous composition comprising acetaminophen, a dissolved oxygen content of maximally 1.0 ppm in a closed container, a pH of 6.3 to 7.3, one or more anti-oxidants, one or more isotonic agents, and one or more pH-adjusting agents

DETAILED DESCRIPTION OF THE INVENTION

The present invention concerns a method for preparing an intravenously administrable aqueous composition comprising acetaminophen, and optionally one or more NSAIDs, preferably ibuprofen, having a dissolved oxygen content of maximally 1.0 ppm, preferably maximally 0.50 ppm, in a closed container. The current invention provides in a second aspect in an intravenously administrable composition comprising acetaminophen with a dissolved oxygen content of maximally 1.0 in a closed container, and optionally one or more NSAIDs, preferably ibuprofen.

It is evident that concerning method can be applied for preparing an intravenously administrable aqueous composition comprising merely acetaminophen as active pharmaceutical ingredient, or for preparing an intravenously aqueous composition comprising both acetaminophen and one or more NSAIDs, preferably ibuprofen, as active ingredients. By applying the methodology of the current invention, a stable solution, suitable for IV injection is obtained.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" and "approximately" as used herein referring to a measurable value such as a parameter, an amount, a temporal duration, and the like, is meant to encompass variations of +/−5% or less, preferably +/−3% or less, more preferably +/−2% or less, even more preferably +/−1% or less, and still more preferably +/−0.1% or less of and from the specified value, in so far such variations are appropriate to perform in the disclosed invention. However, it is to be understood that the value to which the modifier "about" or "approximately" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

For the purpose of the current invention, the term "aqueous" is to be understood as a solution comprising water.

For the purpose of the current invention, the term "atmospheric" is to be understood as the atmosphere of the space in which a compounding vessel is placed. For evident reasons, the atmospheric pressure and air in the description of the present invention are supposed to resemble atmospheric conditions on Earth. Atmospheric air on Earth comprises approximately 20.95 vol.-%, or 209,500 ppm oxygen.

In a first aspect, the present invention provides a method for preparing an intravenously administrable aqueous composition comprising acetaminophen, and optionally one or more NSAIDs, having a dissolved oxygen content in a closed container of maximally 1.0 ppm, and preferably maximally 0.50 ppm.

The method of the current invention comprises the steps of rinsing a compounding vessel with water, preferably water for injection of a temperature of at least 80° C., more preferably at least 90° C. or between 80 and 99° C., thereby heating the vessel and creating an oxygen low environment in said vessel; and dissolving acetaminophen in water for injection in said rinsed vessel, said water for injection is at a temperature of at least 80° C. more preferably at least 90° C. or between 80 and 99° C. The water for injection may optionally, at the time of addition of the acetaminophen in the vessel, already comprise one or more excipients which have been dissolved in said heated WFI present in vessel. Said one or more excipients may be, but not limited to isotonic agents, pH adjusting agents, anti-oxidants, stabilizing agents, preservatives or any combination of the latter. In a further embodiment, one or more NSAIDs such as ibuprofen is added to the composition. Addition of the NSAIDs may occur prior or after addition of acetaminophen to the water for injection.

In a preferred embodiment, the water used for the rinsing of the vessel and further preparation of the composition will originate from a loop, whereby said water is heated to the preferred temperature and which continuously circulates the water.

In particular, the method comprises in a preferred embodiment the following steps:
- rinsing a compounding vessel with water, preferably water for injection (WFI) of at least 80° C., more preferably at least 90° C., thereby heating the vessel and creating an oxygen low environment in said vessel;
- introducing into said compounding vessel one or more excipients, said excipients are preferably one or more isotonic agents and one or more pH-adjusting agents, and optionally one or more NSAIDs (when a combination product is to be produced);
- adding water for injection, whereby said water temperature is more than 80° C., preferably more than 85° C., more preferably above 90° C., more preferably above 95° C., preferably between 80 and 99° C., or between 90 and 99° C. and mixing said introduced excipients and water;
- subsequently dissolving acetaminophen into said mixture; and
- adding one or more anti-oxidants, and optionally one or more pH-adjusting agents to the mixture, thereby obtaining said composition;
- whereby subsequent to the introduction of a constituent of said composition to said vessel, said vessel is closed and put under nitrogen pressure.

A composition having a dissolved oxygen content of less than or equal to 1.0 ppm is favourable for avoiding oxidation and degradation of acetaminophen.

The dissolved oxygen content can be measured by techniques known to a skilled person. The initial or residual dissolved oxygen content can be measured with the aid of an oxygen meter operating according to the Clark principle giving the value of the oxygen content in mg/l. The scale is calibrated between a point zero (reducing solution) and the content at oxygen saturation of distilled water, taking into account the temperature of the medium and the atmospheric pressure. The oxygen content is calculated using a chart as a function of the temperature and the pressure.

More in particular, the present method provides a method for preparing composition comprising acetaminophen, and optionally one or more NSAIDs, preferably ibuprofen, having a dissolved oxygen content of maximally 1.0 ppm, preferably maximally 0.50 ppm when in a closed container.

As discussed above, the method according to the current invention is particularly favourable as it does not require the deoxygenation of the formulation by any means. This is in sharp contrast to the majority of the methods currently described in the art which all require an active step of evacuating or driving the oxygen out the formulation (e.g. bubbling with an inert gas, or use of vacuum, see e.g. U.S. Pat. No. 6,992,218). By making use of the methodology of the current invention, an oxygen low environment is created. Re-oxygenation of the formulation during the production process is prevented by use of a nitrogen pressure in the vessel (preferably the headspace of the vessel).

In a preferred embodiment, pretreating the compounding vessel prior to introducing an ingredient comprises rinsing the compounding vessel, preferably several times, with water at a temperature of 80-99° C., preferably at a temperature of 90-99° C., more preferably at a temperature of between 95° and 99° C. In a preferred embodiment, the water is water for injection (WFI). In a more preferred embodiment, the WFI is provided by a loop which constantly circulates the WFI at a temperature of 80-99° C., preferably 90-99° C., more preferably between 95° C. and 99° C. WFI, especially at such high temperatures, comprises a dissolved oxygen content of less than 0.5 ppm, e.g. approximately 0.20 ppm. As mentioned, the rinsing of the compounding vessel induces preheating of the compounding vessel prior to introducing an ingredient. In a second aspect, during said rinsing steam is generated due to the high temperature of said WFI. Steam comprises a lower density than air and therefore functions as a lifting gas. As a consequence, the generated steam pushes out air present in the headspace of the compounding vessel, thereby leading to a reduction of the oxygen content in the compounding vessel. In this way, pretreating the compounding vessel prior to introducing an ingredient results in both preheating of the compounding vessel, as well as reducing the oxygen content in the compounding vessel.

With the term "headspace of a compounding vessel" is meant, the volume of the compounding vessel which is not occupied by the composition.

According to the requirement of the GMP to avoid microbial growth, WFI should always be circulating at not less than 75° C. in the distribution loop of the manufacturing plant. However, by circulation in a loop and use of WFI at a temperature of 80-99° C., preferably WFI at a temperature of 90-99° C., the risk of microbial growth is even more reduced. In a preferred method, WFI at a temperature of 80-99° C., preferably WFI at a temperature of 90-99° C., more preferably between 95 and 99° C. from a same distribution loop is used for both the rinsing of the compounding vessel and as solvent of the aqueous composition.

Apart from the beneficial effects on the oxygen content in the vessel, preheating of the compounding vessel prior to introducing an ingredient also prevents that the WFI or composition—or intermediate mixture—is cooled down during the preparation process in the compounding vessel. More in particular, preheating the vessel prior to introducing an ingredient allows maintaining the WFI or composition—or intermediate mixture thereof—at an elevated temperature for a longer time. This is advantageous since an elevated temperature of the aqueous solvent or composition—or intermediate mixture thereof—increases the solubility of the ingredients, and in addition, an aqueous composition at a higher temperature dissolves less oxygen, thereby aiding in maintaining the dissolved oxygen content in the composition, and intermediate mixtures thereof, at low levels.

In one embodiment, the compounding vessel is rinsed at least one time with heated WFI. In a preferred embodiment, rinsing of the compounding vessel with WFI at a temperature of 80-99° C., preferably WFI at a temperature of 90-99° C., more preferably 95°–99° C. is repeatedly performed. In a more preferred embodiment, rinsing of the compounding vessel is repeatedly performed until said compounding vessel has a temperature of at least 80° C., and more preferably at least 90° C. Said vessel may be rinsed at least 2 times, more preferably at least 3 times, more preferably at least 4 times, 5 times, 6 times, 7 to 10 times.

Compounding vessels may have a volume capacity of up to 250,000 liter. As a consequence, filling of a compounding vessel can be time-consuming. However, in a preferred embodiment, rinsing of the compounding vessel is performed with a volume of water lower than the volume of the compounding vessel. In a more preferred embodiment, rinsing of the vessel is performed with a volume of water equal to 3 to 20% of the volume of the compounding vessel. In this way, time- and WFI-consumption is substantially reduced. This in turn, allows for a cheaper preparation process.

In another or further embodiment, the compounding vessel may be preheated electronically. Mere preheating of the compounding vessel prior to introducing an ingredient is, however, not sufficient for substantially reducing the oxygen content in the headspace of the compounding vessel. Therefore, electronically preheating the compounding vessel is preferably combined with a pretreating which induces a reduction of the oxygen content in the headspace of the compounding vessel, prior to introducing an ingredient into the compounding vessel.

In a method according to the present invention, the first one or more ingredients and/or WFI are solely introduced into a compounding vessel after pretreating, more in particular rinsing, said compounding vessel such that the oxygen content in the compounding vessel is reduced and the compounding vessel is preheated. In an embodiment, the oxygen content in the compounding vessel is reduced to less than 0.5 ppm prior to introducing an ingredient to said compounding vessel.

Preferably, the compounding vessel is preheated to a temperature of at east 80° C., and more preferably at least 90° C.

After sufficiently pretreating the compounding vessel, one or more excipients, and optionally one or more NSAIDs such as ibuprofen are introduced into the compounding vessel, WFI at a temperature of 80-99° C., preferably WFI at a temperature of 90-99° C., more preferably between 95 and 99° C. is added, and the composition is mixed, preferably until dissolution of all introduced ingredients. Preferably said one or more excipients comprise one or more isotonic agents and one or more pH-adjusting agents.

By preference, the total concentration of the NSAIDs in the composition will be between 2 to 4 mg per ml, more preferably 3 to 4 mg per ml of composition. More preferably, ibuprofen will be present in a concentration of 2 to 4 mg per ml, more preferably 3 to 4 mg per ml.

For an amount of 3.0 mg ibuprofen/ml, 3.85 mg ibuprofen sodium is used.

In a preferred embodiment, said one or more isotonic agents comprises mannitol. Preferably said pH-adjusting agent is hydrochloric acid, more preferably in an amount such that the pH of the composition—after addition of WFI—is 6.3-7.3.

While introducing the WFI at a temperature of 80-99° C., preferably WFI at a temperature of 90-99° C., more preferably 95 to 99° C. into the compounding vessel, the vessel is left open to prevent the building up of an overpressure in the headspace of the vessel. In addition, generation of steam during the addition of aqueous solvent at high temperatures creates an outwardly-directed flow which avoids the entrance of atmospheric air entering the vessel. The aqueous solvent is introduced at a steady pace into the vessel in order to avoid turbulence, and thereby dissolution of oxygen in the WFI.

In a preferred embodiment, the compounding vessel is put under nitrogen pressure, subsequent to the introduction of a constituent of said composition into the vessel. In an embodiment, a nitrogen pressure is applied to the compounding vessel, more in particular to the headspace of the compounding vessel, prior to mixing of ingredients introduced into the compounding vessel. Applying a nitrogen pressure to the compounding vessel prevents the re-oxygenation of the formulation in the vessel. As a consequence, dissolution of oxygen in the final or intermediate composition, or an intermediate mixture thereof, is avoided, which is in particular important during mixing of the composition, or an intermediate mixture thereof. Preferably, the nitrogen pressure induces an overpressure of at least 0.1 bar and preferably of maximally 1.0 bar in the compounding vessel as compared to the atmospheric pressure. More preferably, an overpressure of at least 0.1 bar, and preferably of at most 0.5 bar in the compounding vessel as compared to the atmospheric pressure. Evidently, the compounding vessel is closed upon applying the nitrogen overpressure to the headspace of the compounding vessel. It is emphasized that an overpressure to the headspace of the compounding vessel is applied by introducing nitrogen gas from the upper side, more preferably from the top side, of the vessel. In this way the nitrogen gas does not pass through the aqueous composition, or an intermediate mixture thereof, and dissolution of oxygen into the composition, or an intermediate composition thereof, is avoided.

Preferably, the overpressure in the headspace of the compounding vessel is applied by introducing nitrogen gas. More preferably the overpressure in the headspace of the compounding vessel is applied by introducing filtered nitrogen gas. Preferably, the nitrogen gas is 0.22 μm filtered nitrogen gas.

After mixing of the introduced excipients, and if a combination product is produced, the addition of one or more NSAIDs such as ibuprofen, with the introduced WFI, the compounding vessel is opened and acetaminophen is introduced into the compounding vessel. After introduction of acetaminophen, the vessel is closed as quickly as possible to avoid the entrance of atmospheric air, and the constituents are mixed, preferably until all ingredients are dissolved. The applied overpressure in the compounding vessel will result in an outwardly outwardly-directed flow of nitrogen gas occurs when opening the vessel; said flow prevents entrance of atmospheric air. Preferably, acetaminophen is introduced within the time interval in which the overpressure in the headspace is equilibrated to the atmospheric pressure.

In a preferred embodiment, after introducing acetaminophen and prior to mixing, an overpressure is reapplied to the headspace of the vessel by introducing nitrogen gas from the upper side of the vessel. Preferably said overpressure is 0.1 to 1.0 bar, and more preferably between 0.1 and 0.5 bar.

In a preferred embodiment, an amount of acetaminophen of 9.8 to 10.2 mg, more preferably 10.0 mg/ml, is introduced into the compounding vessel.

Advantageously, the aqueous mixture is not cooled prior to admixture of the one or more active principles, which constitutes not only a gain in the preparation time of the formulation as there is no need to use heat exchangers to cool the aqueous solvent, but also permits to obtain a suitable oxygen concentration. Addition of the oxygen sensitive acetaminophen and anti-oxidant to a medium with lowered oxygen content, as opposed to deoxygenation of the solution already containing these ingredients, has the advantage that the detrimental effects of oxygen are kept minimal, and that potentially present anti-oxidant is not prematurely consumed and remains available to provide long term storage stability. Preferably, the temperature of the mixture is preferably held at least at 80° C., and more preferably at least at 90° C. prior to admixture of the active principle.

In a preferred embodiment, WFI for the final volume of the composition is added after introducing acetaminophen and mixing, followed by mixing of the mixture. More preferably, an overpressure is applied after adding WFI for the final volume and prior to mixing of the mixture.

The mixture comprising acetaminophen, and optionally one or more NSAIDs, is then cooled down. Preferably by circulating cold water in the double jacket of the compounding vessel to speed up the cooling process.

In a preferred embodiment of a method according to the invention, one or more anti-oxidants are added to the cooled aqueous mixture. Anti-oxidants for use in the invention are preferably selected from the list of a sulphite, or sulphite derivative, a thiolic substance such as, for example, cysteine, acetylcysteine, dithiothreitol or alpha-thioglycerol, thiomalic acid, thioglycerol, methionine; a hydroxylated substance such as ascorbic acid, iso-ascorbic acid, mannitol, sorbitol, an ethylenically unsaturated substance such as sorbic acid, undecylenic acid or fumaric acid or a hydroxy polycarboxylic acid, or a reducing sugar such as trehalulose, maltulose or isomaltulose. In a preferred embodiment the anti-oxidant is selected from cysteine and acetyl cysteine. Cysteine is preferably cysteine hydrochloride. By preference, the monohydrate form is used. By the term "(acetyl) cysteine" as used herein, is meant acetylcysteine and/or cysteine. Acetyl cysteine or cysteine as anti-oxidant suppresses the generation of unwanted degradation products of acetaminophen by oxidation. In spite of the risk that their use will provide yellow solutions, they are preferred as they can reduce the risk of acetaminophen toxicity.

In a more preferred embodiment, the anti-oxidant is added at a temperature of at most 40° C. to avoid degradation of the acetyl cysteine or cysteine at higher temperatures. Preferably the mixture comprising acetaminophen, and optionally one or more NSAIDs, is cooled to a temperature of at most 40° C., preferably to 39° C. or 38° C., 37° C., 36° C. or 35° C., prior to the addition of acetyl cysteine or cysteine. Preferably the addition of cysteine or acetyl cysteine to the mixture does not change said pH of 6.3-7.3. In a preferred embodiment, the aqueous composition has a pH of 6.3 to 7.3 prior to and after addition of the anti-oxidant. Preferably the pH of the final product is around 6.6. In a preferred embodiment, when the mixture prior to introduction of one or more anti-oxidants does not have a pH which falls within a range as mentioned above, then one or more pH-adjusting agents may be introduced into the compounding vessel upon introducing the one or more anti-oxidants.

In a preferred embodiment an overpressure is applied to the headspace of the compounding vessel every time the compounding vessel is opened, and prior to mixing the composition, or an intermediate composition thereof, during the preparation method in the compounding vessel. This is advantageous as the overpressure is equilibrated to the atmospheric pressure every time the compounding vessel is opened. The overpressure avoids entrance of atmospheric air into the headspace when opening the vessel, and minimizes dissolution of oxygen into the composition, or an intermediate composition thereof, during mixing. It is deemed evident that, as a consequence thereof, introducing one or more ingredients into the vessel has to be performed as quickly as possible after opening the vessel such that it can be closed shortly after its opening in order to leave the vessel open only for a limited period of time.

In a preferred embodiment, the mixture to which pharmaceutically active ingredients—acetaminophen, and optionally one or more NSAIDs—are added, has a pH of 6.0-8.0, preferably 6.2-7.5, preferably 6.3 to 7.3. In a more preferred embodiment, the mixture has a pH of 6.4-6.6. In a preferred embodiment, the final composition has a pH of 6.4-6.6. The term "final composition", refers to the composition to be filled into receptacles, preferably vials, and ready for use. It was found advantageous to start at the low end of the pH range. Preferably, the final product has a pH on storage that remains stable or may evolve within the specified range. This pH range avoids the precipitation of ibuprofen and degradation of acetaminophen at the same time.

The pH may be adjusted to a desired level prior to admixing active principles using one or more pH-adjusting agents. In a preferred embodiment, the pH of the mixture is 6.3 to 7.3 prior to introducing acetaminophen, and optionally one or more NSAIDs, preferably ibuprofen. Preferably, the pH of the mixture is at 6.3 to 7.3 after introducing acetaminophen, and optionally one or more NSAIDs, preferably ibuprofen. Hence, in a preferred embodiment, the intravenously administrable composition comprises pH-adjusting agents. In a more preferred embodiment, the pH-adjustment agents used in a method according to the invention, are hydrochloric acid and sodium hydroxide.

The pH of the composition may be buffered. Suitable buffering agents may include one or more of citric acid, sodium citrate, sodium phosphate, potassium citrate, and the like. Preferably the buffering agent is disodium phosphate.

In a preferred embodiment of a method and composition of the invention the composition comprises one or more isotonic agents. Use of one or more isotonic agents has the advantage that an osmotic pressure is created in the region of that of physiological saline. An isotonic agent herein may be a polyol, a sugar, a linear or cyclic glucitol having from 2 to 10 carbon atoms selected from mannitol, sorbitol, inositol, glucose and glycerol. A preferred isotonic agent is mannitol.

More pharmaceutically acceptable excipients may be present. However, in a preferred embodiment there are no additional excipients present.

The mass ratio (w/w) of the one or more isotonic agents to acetaminophen, for instance mannitol: acetaminophen is preferably 2 to 6:1, more preferably 3 to 5:1, most preferably around 4:1. Preferably the one or more isotonic agents are added to the aqueous solution, preferably water, prior to the introduction of acetaminophen, and optionally prior to the introduction of.

In a preferred embodiment, the pH-adjusting agents used in methods according to the invention, are sodium hydroxide-disodium phosphate salt and acetyl cysteine or cysteine. In a more preferred embodiment, the pH adjustment agents are hydrochloric acid and sodium hydroxide.

In a preferred embodiment the final pH of the formulation is from 6.3 to 7.3. Preferably the final pH is 6.4 to 6.9, more preferably 6.5 to 6.8. In a preferred embodiment of a process of the invention the aqueous composition as obtained has a pH around 6.6. Preferably the pH is 6.3 to 7.3 after a shelf-life of at least six months.

Preferably, the mass ratio (w/w) of cysteine hydrochloride to acetaminophen in the final formulation is 0.010 to 0.040: 1, preferably 0.020 to 0.030:1, preferably 0.025:1.

Preferably, the mass ratio (w/w) of acetyl cysteine or cysteine hydrochloride to ibuprofen in the final formulation is 0.20 to 0.40:1, preferably 0.10 to 0.20:1, preferably 0.08:1.

For example, in a formulation and method as defined herein, (acetyl)cysteine hydrochloride may be present in the final formulation in an amount preferably between 0.015% and 0.05%, preferably around 0.025% (w/v).

The obtained composition may be filtered, for example in a filtration unit.

As during compounding, oxygen contact or oxygen ingress into the aqueous solution during filling/packaging and/or storage is preferably avoided.

Preferably the containers, preferably vials, for the composition comprising acetaminophen, and optionally one or more NSAIDs, preferably ibuprofen, are washed with warm water prior to filling. In particular, the containers may be washed with WFI at a temperature of above 80° C., more preferably between 80-99° C., preferably WFI at a temperature of 90° C.-99° C. WFI at such temperature has a low dissolved oxygen content. It is particularly suitable to take up oxygen from the receptacle and reduce its oxygen content.

In a subsequent step, the washed containers may be dried. Preferably drying is carried out with dry air. Dry air with low moisture content, again minimizes re-uptake of oxygen by the packaging, and later on by the acetaminophen-comprising composition, or by the composition comprising acetaminophen and one or more NSAIDs, preferably ibuprofen.

After drying the washed and/or dried containers may be rinsed with nitrogen. Preferably nitrogen low in oxygen is used.

Following the pre-treatment of the containers, said containers are filled with the acetaminophen-comprising composition, or with the composition comprising acetaminophen and one or more NSAIDs, preferably ibuprofen.

The compounding procedure preferably provides an aqueous composition comprising acetaminophen, or acetaminophen and one or more NSAIDs, preferably ibuprofen, prior to filling/packaging with a dissolved oxygen content of below 1.0 ppm, preferably below 0.5 ppm, more preferably around 0.4 ppm.

An intravenously administrable aqueous composition comprising acetaminophen or acetaminophen and one or more NSAIDs, preferably ibuprofen, prepared according to a method of the present invention has less than or equal to 1.0 ppm, more preferably less than or equal to 0.5 ppm dissolved oxygen during filling.

Preferably the containers are sealed under vacuum; preferably said vacuum is between 450 mbar and around 1 bar.

The containers are then sealed, for instance by adding a stopper, sealing under vacuum and providing a crimping cap covering the stopper.

These bottles can subsequently be heat-sterilised, for instance for 15 minutes at 121° C. It will be understood to a person skilled in the art that other sterilisation methods equally apply.

In a preferred embodiment, a method according to the invention further comprises in specified order the steps of:
washing said containers with WFI at a temperature of 80° C.-100° C.,
drying said washed containers, preferably with dry air,
rinsing said washed containers, preferably with nitrogen,
filling said nitrogen washed container with the aqueous composition comprising acetaminophen or acetaminophen and one or more NSAIDs, preferably ibuprofen;
sealing said container under vacuum, preferably between 450 mbar and around 1 bar.

In a more preferred embodiment, said vacuum sealed product container comprises a stopper made of an elastic material covered by a crimping cap.

In a preferred embodiment said elastic material of the stopper is rubber, preferably a butyl rubber or halo butyl rubber. These rubber types have a low oxygen transmission coefficient. Preferably the stopper is sealed by an aluminium crimping caps. Preferably said vial is closed with a (halo) butyl rubber stopper, preferably bromobutyl rubber, and sealed by an aluminium caps.

Preferably the container used to obtain a product according to an embodiment of the invention is a vial; preferably a colourless type H glass Eur. Ph. 3.2.1 vial.

In a preferred embodiment according to the invention the closed product container has reduced pressure inside. Preferably the pressure is reduced to allow the addition of solvent for injection to the closed system, e.g. by means of penetrating the closure with a needle. Preferably the reduced pressure is between 450 mbar and around 1 bar.

In a preferred embodiment the container comprises a vial with a blow back inside of the flange. The blow back improves the fit of the stopper and avoids that the stopper pops out of the vial. The flange of the vial and the dimensions of the stopper are chosen in a way to guarantee a good fit of the stopper during stoppering and sealing. It is preferred to have a blow back with dimensions in size to provide sufficient sealing surface between the vial and the stopper in order to keep a vacuum in the vial as long as possible.

Preferably the container/closure system has a blow back; particularly when applying reduced pressure. In comparison to systems having no blow back, blow back systems are very tight and the risk of influx of air and thus oxidation can be reduced.

It is evident that concerning method can also be applied for preparation of an intravenously administrable composition comprising acetaminophen without one or more NSAIDs such as ibuprofen.

As discussed above, methods known in the art describe preparation methods comprising deoxygenation of the composition. Known from the literature, this can be to be time-consuming. Furthermore, implementation of deoxygenation of the composition indicates that the dissolved oxygen content of the composition prior to deoxygenation is insufficiently low to prevent oxidation of acetaminophen, and thus, that anti-oxidant can be prematurely consumed or that some of the acetaminophen in the composition could be affected by the insufficiently low dissolved oxygen content prior to deoxygenation of the composition. A time-interval in which acetaminophen is subjected to an insufficiently low oxygen content is not observed in a method according to the present invention. More in particular, the dissolved oxygen content of the composition increases continuously during the preparation method according to the present invention.

The present invention therefore provides in a more efficient and less complex, preparation method of composition comprising acetaminophen, and optionally one or more NSAIDs, preferably ibuprofen.

In a second aspect, the present invention provides an intravenously administrable aqueous composition comprising acetaminophen, and optionally one or more non-steroidal anti-inflammatory drugs (NSAIDs), preferably ibuprofen, having a dissolved oxygen content of maximally 1.0 ppm, preferably maximally 0.5 ppm in a closed container.

An oxygen content of less than or equal to 1.0 ppm, preferably less than or equal to 0.5 ppm, is favourable for avoiding oxidation of acetaminophen, especially in the presence of an NSAID, preferably ibuprofen.

It is known from the prior art that acetaminophen is susceptible to oxidation, and that oxidation products of acetaminophen lead to formation of undesired colored compounds. Compositions according to the present invention comprise a dissolved oxygen content of maximally 1.0 ppm, preferably maximally 0.5 ppm, and therefore show a reduction in the oxidation rate of acetaminophen. As a consequence, compositions according to the present invention comprise a long durability and storage ability, and comprise very low concentrations of undesired acetaminophen oxidation products.

In a preferred embodiment, a composition according to the present invention comprises 9.8 to 10.2 mg acetaminophen, preferably 10 mg acetaminophen.

Preferably, a composition according to the present invention comprises one or more pharmaceutically acceptable excipients. More preferably, a composition according to the present invention comprises one or more anti-oxidants, one or more isotonic agents, and/or one or more pH-adjusting agents.

In an embodiment, the one or more anti-oxidants are selected from the group of acetyl cysteine or a cysteine, such as cysteine hydrochloride.

In an embodiment, the one or more isotonic agents are selected from the group of mannitol, sorbitol, inositol, glucose and glycerol.

In an embodiment, the one or more pH adjusting agents are chosen from the group of hydrochloric acid and sodium hydroxide.

Preferably an aqueous composition according to the present invention has an osmolality of between 285-320 mOsmol/l as determined by point depression according to USP 788.

From literature, it is known that acetaminophen is liable to undergo hydrolysis. The rate of degradation of acetaminophen increases with increasing temperature and light. This rate is minimal at a pH in the region of 6.

In a preferred embodiment, an aqueous composition according to the present invention comprises a pH from 6.3 to 7.3, preferably the pH is 6.4 to 6.9, more preferably 6.5 to 6.8, and most preferably the composition has a pH of around 6. In this way, the degradation rate of acetaminophen in aqueous compositions according to the present invention is substantially reduced.

In an embodiment, a composition according to the present invention may further comprise one or more NSAIDs, preferably ibuprofen. In a preferred embodiment, the composition comprises 2 to 4 mg, more preferably 3 to 4 mg ibuprofen expressed per ml of said composition, and preferably 3 mg ibuprofen expressed per ml of said composition.

Ibuprofen is preferably introduced in the form of ibuprofen sodium.

In a preferred embodiment said composition has a storage stability of at least 6 months, preferably at least 9 months, more preferably at least 12 months, most preferably 24 months, based on the acetaminophen- and acetaminophen/ibuprofen-content as measured by HPLC in accordance with European Pharmacopeia 2.2.29 and USP 621.

In a preferred embodiment, the (acetyl)cysteine amount in the composition at the completion of its preparation is at least 80%, preferably at least 85%, most preferably at least 90%, of the initial amount added.

In a preferred embodiment, the (acetyl)cysteine hydrochloride content is at least 40% of the initial amount added, preferably at least 50%, preferably at least 75%, during the shelf-life of the composition. A low consumption of (acetyl)cysteine is indicative of a low exposure to oxygen during the period of storage.

In a preferred embodiment, an aqueous composition according to the present invention is obtainable by a method according to the present invention. In a most preferred embodiment, an aqueous composition according to the present invention is obtained by a method according to the present invention.

In a further embodiment said composition is for use as a medicament. Especially important for its suitability in the pharmaceutical and medical field is the pH of the composition.

In a more preferred embodiment said composition is for use in the treatment of pain and/or of inflammation.

In a preferred embodiment, its pH makes the composition particularly suitable for administration by intravenous injection. In a most preferred embodiment said composition is for administration by intravenous injection.

The compositions thus obtained may be distributed into ready-to-use hermetically stoppered or sealed, bags, pouches or bottles.

By preference, the composition is produced by the methodology as described above. More in particular, the composition is described by the following methodology:

A formulation according to an embodiment of the invention can generally be prepared as follows. Prior to introducing one or more ingredients, a compounding vessel is pretreated such that the vessel is preheated and the headspace of the compounding comprises a reduced oxygen content. Preferably said pretreatment comprises rinsing the compounding vessel several times with WFI at a temperature of 80-99° C., preferably WFI at a temperature of 90-99° C. until the compounding vessel has a temperature of at least 80° C., preferably at least 90° C.

After pretreating the vessel, the vessel is opened, one or more excipients, and optionally one or more NSAIDs, are introduced into the vessel. Then, WFI at a temperature of 80-99° C., preferably WFI at a temperature of 90-99° C., is added, and the vessel is closed. Nitrogen gas is introduced from the upper part of the compounding vessel to apply an overpressure to the headspace of the compounding vessel, prior to mixing the composition. Preferably, said one or more excipients comprise one or more isotonic agents, one or more pH-adjusting agents and a buffering agent. After ceasing the mixing of the composition, the vessel is opened, acetaminophen is introduced into the composition, the vessel is closed and a nitrogen overpressure is applied to the headspace of the compounding vessel prior to mixing the composition. Preferably, the temperature of the composition is kept at least at 80° C., and more preferably at least at 90° C. prior to admixing the active principles. After introducing acetaminophen and mixing the composition, said composition is cooled, preferably to below 40° C. When cooled, the vessel is opened, disodium phosphate dihydrate and sodium hydroxide to arrive upon a pH of 6.3-7.3, are added to the composition, the vessel is closed, and a nitrogen overpressure is applied prior to mixing of the composition. Then, the vessel is opened, cysteine hydrochloride is introduced, the vessel is closed and a nitrogen overpressure is applied prior to mixing of the composition. The composition is filtered, and the filtered composition is filled into containers.

Advantageously, the introduction of ingredients is performed as quickly as possible to avoid the entrance of atmospheric air into the headspace of the compounding vessel.

The present inventor has found that the indicated method allows preparation of acetaminophen, and optionally the combination of acetaminophen and one or more NSAIDs, preferably ibuprofen, in aqueous composition in a less complex, more cost-efficient and less time-consuming way, and thereby at the same time reducing acetaminophen, and preferably ibuprofen, degradation.

Evidently, a method according to the present invention can be performed both with and without introducing one or more NSAIDs.

The invention is described in greater detail in the examples below, which are given as non-limiting illustrations. In these examples, the temperature is room temperature or is expressed in degrees Celsius, and the pressure is atmospheric pressure. The water and all the reagents used are of injectable grade.

Moreover, all the examples form an integral part of the invention, as does any characteristic of the description including the examples, which appears to be novel with respect to any prior art, in the form of a general characteristic rather than of a particular characteristic of the example.

EXAMPLES

In the following, examples are intended to further clarify the present invention, and are nowhere intended to limit the scope of the present invention.

1. Preparation of Intravenously Administrable Composition Comprising Acetaminophen According to an Embodiment of the Present Invention Step 1: Weighing of the Components More in particular, acetaminophen drug substance and excipients were separately weighed under laminar air flow in class C. Every ingredient was dispensed into double plastic bag duly identified and weight was double checked.

Step 2: Compounding of the Composition.

Operations of adding of ingredients should be performed as fast as possible.

An empty compounding vessel which was opened, was rinsed several times with WFI at the temperature at which it was in the loop without cooling, which was at least 90° C. Said heated WFI comprised a dissolved oxygen content of 0.24 ppm. During the rinsing with the heated WFI, the vessel was preheated to a temperature of 90° C. and steam was generated in the headspace of the compounding vessel. Said steam induced an overpressure which extruded air- and therewith oxygen—from the headspace of the compounding vessel. As a consequence, the oxygen content in the headspace of the compounding vessel was substantially reduced.

Mannitol and hydrochloric acid 1M for pH 6.3-7.3 of batch formula were introduced into the pretreated vessel and 95% of the final required volume of WFI at a temperature of at least 90° C. was added. The vessel was closed, put under overpressure by introducing nitrogen gas from the upper side of the vessel (preferred pressure between 0.1 and 1 bar), and the composition was mixed until complete dissolution of all components.

After mixing, the vessel was opened, acetaminophen was introduced, the vessel was closed, and an overpressure was again applied to the headspace of the compound vessel by introducing 0.22 μm-filtered nitrogen gas from the upper side of the vessel, prior to mixing until all components were completely dissolved.

After mixing the composition, the vessel was opened, WFI-volume required for the final volume of the composition was added from the loop at a temperature of at least 90° C., the vessel was closed and put under an overpressure by introducing nitrogen gas from the upper side of the compounding vessel prior to mixing.

Under mixing, the temperature of the preparation was cooled till 38° C. by circulating water in the double jacket of the vessel.

The vessel was opened, disodium phosphate dehydrate and sodium hydroxide for a pH of 6.3-7.3 of batch formula was introduced into the vessel, the vessel was closed, and put under an overpressure of nitrogen gas from the upper side of the vessel, prior to mixing the mixture until complete dissolution of the components.

After mixing, the vessel was opened, cysteine hydrochloride monohydrate was introduced, the vessel was closed, and put under an overpressure by introducing nitrogen gas from the upper side of the vessel prior to mixing until complete dissolution of the components.

End of compounding of the composition.

Maximal duration time of the compounding of the composition (process time): 4 hours.

Step 3: Cleaning-Depyrogenation of Empty Vials, Stoppers, Filtration-Filling of the Composition into the Vials, Stoppering (Closing) and Sealing (Crimping) of Vials.

These operations are performed in-line:
After compounding of the composition in the compounding vessel, the valve connecting the compounding vessel to the filter is open as well as the valve connecting the filter to the intermediate vessel. The composition is filtered by 0.22 μm filter.
At the same time, in continuous basis, vials are cleaned and depyrogenated.
Stoppers are cleaned, depyrogenated and finally rinsed with WFI by the supplier.
Once filling starts, the composition goes from the compounding vessel to the intermediate vessel on the filling machine throughout the 0.22 μm filter. The composition is taken from the intermediate vessel by the filling machine in order to be filled into the vials.
The composition is filled into the vials as follows:
Empty vials are flushed by nitrogen
The composition is filled into the vials
Air in the head space of vials is flushed nitrogen
Vials are closed by the stoppers under vacuum
In case of filling stop more than one minute, all filled vials that are not closed by the stoppers are discarded.
Closed vials on the filling machine are driven in conveyer in class C to the sealed machine placed in front in the sealing room where are sealed by aluminium caps.

The dissolved oxygen content of the composition in the filled vials was below 0.5 ppm.

Maximal duration time of cleaning-depyrogenation of empty vials, filtration-filling of the composition into the vials, stoppering (closing) and sealing (crimping) of vials (process time): 10 hours.

Step 4: Sterilisation at End Point

Sterilization of the composition filled in the vials is performed in autoclave.

Step 5: Visual Inspection

Visual inspection of 100% of sterilised vials is performed by automatic machine.

Step 6: Print of Carton Boxes

Carton boxes are printed with batch number and expiry date by automatic printer machine.

Step 7: Labelling and Final Packaging

By automatic machine, labels of the vials are printed with batch number and expiry date, vials are labelled and are packed in carton box.

The relevant manufacturing steps are performed quickly and without any unnecessary interruption in order to reduce incorporation of air in the compounding vessel and to keep the composition at the required temperatures i.e. between 65° C. and 98° C. for the admixing steps before acetyl cysteine or cysteine are added; and below or at 38° C. for the acetyl cysteine or cysteine addition part.

The air inside the headspace of the compounding vessel was compressed from the upper side of the vessel by 0.22

μm filtered nitrogen pressure. The nitrogen pressure applied on the composition in the compounding vessel pushes the composition through the filter.

TABLE 1

Formulation 1

| Name of ingredient | Unit formula 100 ml | Formula per 1 ml |
|---|---|---|
| Acetaminophen | 1.0 g | 10 mg |
| Mannitol | 3.2850 g | 32.850 mg |
| Hydrochloric acid | to pH = 6.4 | to pH = 6.4 |
| Cysteine hydrochloride monohydrate | 25.0 mg | 0.25 mg |
| Disodium phosphate dihydrate | 13.0 mg | 0.13 mg |
| Sodium hydroxide | to pH = 6.6 | to pH = 6.6 |
| WFI | q.s. ad 100.0 ml | q.s. ad 1.0 ml |
| Nitrogen Low Oxygen | q.s. | q.s. |

2. Preparation of an Alternative Liquid Pharmaceutical Formulation According to an Embodiment of the Present Invention, Comprising Both Acetaminophen and Ibuprofen An alternative formulation was prepared according to the method described under Example 1. In this method, a formulation comprising both acetaminophen and ibuprofen was prepared. Therefore, ibuprofen sodium dehydrate was added at the same time as when mannitol and hydrochloric acid were added. Opposed to the detailed example presented above, the dissolved oxygen content in following example is measured to one decimal. As a consequence, the margin of error is larger than in example 1.

Analysis of bulk composition before filtration demonstrated a dissolved oxygen content of 0.2 ppm, whereas the dissolved oxygen content in the first filled vials after filtration was 0.4 ppm. Therefore, an increase in dissolved oxygen content was observed.

TABLE 2

Formulation 2

| Name of ingredient | Quantity in Kg | Formula per 1 ml (mg) |
|---|---|---|
| Ibuprofen sodium | 6.55 | 3.85 |
| Acetaminophen | 17.00 | 10.00 |
| Mannitol | 55.85 | 32.85 |
| Hydrochloric acid 1M (up to pH 6.3-7.3) | 0.204 L | 0.00013 ml |
| Sodium hydroxide 1M (up to pH 6.3-7.3) | 1.711 L | 0.00101 ml |
| Cysteine hydrochloride monohydrate | 0.4250 | 0.25 |
| Disodium phosphate dihydrate | 0.2210 | 0.13 |
| Nitrogen Low Oxygen | 245.0 | 144 |
| WFI | 1700 | 1 ml |

3. Importance of Rinsing A formulation was prepared almost exactly according to the method described in claim 1. The only difference in the preparation method as compared to the preparation method in example 1, was the amount of sequential rinsing steps during pretreating the headspace of the compounding vessel. More in particular, the vessel was rinsed merely two times with WFI at the temperature it was in the loop without cooling, which was not less than 90° C. The rinsing water comprised a dissolved oxygen content of 0.24 ppm. After this rinsing, the temperature of the vessel was merely 56° C.

The preparation method was further performed exactly as described in example 1.

The dissolved oxygen content of the composition after introducing and mixing of mannitol, sodium dihydrate, hydrochloric acid 1M for pH 6.3-7.3 of batch formula and 95% of the WFI-volume was 0.56 ppm, compared to 0.34 ppm oxygen in example 1.

After introducing acetaminophen and WFI for the final volume, the composition comprised a dissolved oxygen content of 0.49 ppm, and had a temperature of merely 73° C.

At the end of the compounding process, the dissolved oxygen content of the composition was 0.50 ppm, and after filtration-filling of the composition into vials (including stoppering and sealing), the dissolved oxygen content of the composition was 0.52 ppm.

4. Storage Stability Data

An ibuprofen/acetaminophen combination product was prepared as follows:

An empty compounding vessel was rinsed three times with WFI at the temperature that it was in the loop without cooling, which was 97.8° C. As a consequence, air in the vessel was extruded by an overpressure due to generated steam, and the vessel was heated to a temperature of 92.3° C. The WFI used for rinsing of the vessel comprised a dissolved oxygen content of 0.24 ppm.

To the rinsed, preheated and empty compounding vessel were added mannitol, ibuprofen, hydrochloric acid 0.1N for obtaining a pH of 6.3 to 7.3 and WFI at a temperature of 97.8° C. and comprising a dissolved oxygen content of 0.24 ppm. The quantity of hydrochloric acid to be added was calculated in advance and is such that the desired pH is maintained 6.3-7.3. The compounding vessel was closed and the few air remaining in the headspace of the vessel was compressed by nitrogen introduced from the upper side, at 1.2-1.5 bar, followed by stirring. At this point in the preparation method, the composition comprised an oxygen content of 0.35 ppm.

The compounding vessel was quickly opened and acetaminophen was quickly added without stirring. The vessel was closed and remaining air in the headspace of the vessel was compressed by nitrogen introduced from the upper side of the vessel, at 1.2-1.5 bar, followed by stirring. The dissolved oxygen content of the composition was 0.36 ppm.

The composition was cooled to a temperature below 40° C. The temperature reached, the mixing vessel was quickly opened and sodium hydroxide 0.1 N and disodium phosphate were quickly added without stirring. Compounding vessel was closed and the few air remaining in the headspace of the vessel was compressed by nitrogen introduced from the upper side of the vessel, at 1.2-1.5 bar, followed by stirring. The dissolved oxygen content of the composition comprised 0.36 ppm.

The quantities of sodium hydroxide and disodium phosphate to be added were calculated in advance and are such that the desired pH is maintained at 6.3-7.3 after the addition of cysteine.

The compounding vessel was quickly opened and acetyl cysteine or cysteine was quickly added without stirring. The compounding vessel was closed and the air remaining in the headspace of the vessel was compressed by filtered nitrogen introduced from the upper side of the vessel, at 1.2-1.5 bar, followed by stirring. At this point, the composition comprised a dissolved oxygen content of 0.36 ppm.

Samples were stored and analyzed after set time-intervals. The results for the compositions of pH 6.6 stored at a temperature of 25+/−2° C. at a relative humidity of 40+/−5% are summarized in Table 8. Those of pH 7.0 stored at a temperature of 25+/−2° C. at a relative humidity of 40+/−5% are provided in Table 9. Further results from a storage stability test on samples prepared as previously described, are provided in Table 10. These samples were kept at a temperature of 25+/−2° C. and a relative humidity of 40+/−5%. Those of pH 6.4 stored at a temperature of 25+/−2° C. at a relative humidity of 60+/−5% are provided in Table 11.

A series of analysis was performed on the sample. The appearance of a composition was determined by visual inspection according to USP 641, pH values were determined using potentiometry using USP 791, coloration was determined following Eur. Ph 2.2.2 point depression USP 785, sub visible particles were assessed using a light obscuration particle count method USP 788, cysteine.HCl*$H_2O$, ibuprofen and acetaminophen were identified using liquid chromatography USP 621. Acetaminophen content was determined by HPLC, Eur. Ph. 2.2.29, 0049. Ibuprofen content and amount of cysteine HCl*$H_2O$ are determined by liquid chromatography USP 621. Acetaminophen impurities were determined using Eur. Ph 2.2.29, 0049. Ibuprofen impurities were determined using Eur. Ph 2.2.29.

From the data in both tables it can be seen that a clear liquid composition is provided. The physical appearance is obtained even after twelve months of storage and more. The cysteine content remains high and essentially stable over time. Impurity levels are very low for both acetaminophen and ibuprofen, in spite of the pH considered disadvantages for the active principles when present alone.

The storage stability test results indicate that a product shelf-life of two years is feasible. It can be concluded that the invention provides stable ibuprofen/acetaminophen combination products of pH 6.3-7.3.

5. Compatibility

To test the compatibility of ibuprofen and acetaminophen in combination, the following experiment was performed.

The pH 8.80 of a composition of 3.85 mg/ml of sodium ibuprofen $2H_2O$, equivalent to 3 mg/ml of ibuprofen, in water is gradually decreased and the absence or presence of precipitation is observed as an indication of solubility/compatibility. The results are noted down and summarized in Table 3. Precipitation of ibuprofen is observed once pH is at 5.75. The Ibuprofen compositions were stored for 1 month at 25° C. They were again observed for signs of precipitation. The results are summarized in Table 4. Ibuprofen compositions at pH 6 showed precipitation, whereas in compositions of ibuprofen at pH 6.2, precipitation was absent.

TABLE 3

Dissolution of sodium ibuprofen $2H_2O$ alone in water

| | pH | | | | | | | | | | | |
|---|---|---|---|---|---|---|---|---|---|---|---|---|
| | 3 | 4 | 5 | 5.5 | 5.8 | 6 | 6.2 | 6.4 | 6.6 | 6.8 | 7 | 7.5 |
| Dissolved | No | No | No | No | Yes | Yes | Yes | Yes | Yes | Yes | Yes | Yes |

TABLE 4

Dissolution of sodium ibuprofen $2H_2O$ in water after 1 month storage at 25° C.

| | pH | | | | | | | |
|---|---|---|---|---|---|---|---|---|
| | 5.8 | 6 | 6.2 | 6.4 | 6.6 | 6.8 | 7 | 7.5 |
| Dissolved | No | No | Yes | Yes | Yes | Yes | Yes | Yes |

In a further experiment the dissolution of sodium ibuprofen $2H_2O$ was studied in combination with acetaminophen at a concentration of 10 mg acetaminophen per liter. The results at varying pH are summarized in Table 5. The results after one month of storage at 25° C. are provided in Table 6.

TABLE 5

Dissolution of sodium ibuprofen $2H_2O$ in the formulation 3 mg/ml Acetaminophen 10 mg/ml Ibuprofen

| | pH | | | | |
|---|---|---|---|---|---|
| | 6.2 | 6.3 | 6.4 | 6.6 | 7 |
| Dissolved | Yes | Yes | Yes | Yes | Yes |

TABLE 6

Dissolution of sodium ibuprofen $2H_2O$ in the formulation Acetaminophen - Ibuprofen - 1 month

| | pH | | | | |
|---|---|---|---|---|---|
| | 6.2 | 6.3 | 6.4 | 6.6 | 7 |
| Dissolved | No | Yes | Yes | Yes | Yes |

TABLE 7

Dissolution of sodium ibuprofen $2H_2O$ in the formulation Acetaminophen - Ibuprofen - 6 months, 25° C.

| | pH | | | |
|---|---|---|---|---|
| | 6.3 | 6.4 | 6.6 | 7 |
| Dissolved | Yes | Yes | Yes | Yes |

The amount of acetaminophen was studied at varies points in time and for different pH's. Data showed that minimal degradation of acetaminophen occurred at the pH range 6.3-7.3.

From the above it is concluded that the combination of ibuprofen and acetaminophen is stable with a pH range of 6.3-7.3.

TABLE 8 storage stability date 3 mg/ml ibuprofen 10 mg/ml acetaminophen with cysteine (pH 6.6, 25 +/− 2° C., 40 +/− 5% relative humidity)

| Analysis | Specification | 1 month | 2 months | 3 months | 6 months | 9 months | 12 months | 15 months | 18 months | 24 months |
|---|---|---|---|---|---|---|---|---|---|---|
| Appearance of composition | Clear liquid | clear liquid | clear liquid | clear liquid | clear liquid | clear liquid | clear liquid | clear liquid | clear liquid | clear liquid |
| pH value | To be determined | 6.66 | 6.66 | 6.69 | 6.70 | 6.75 | 6.72 | 6.79 | 6.81 | 6.83 |
| Coloration | ≤Y 6 | <Y6 | <Y6 | <Y6 | <Y6 | <Y6 | <Y6 | <Y6 | <Y6 | <Y6 |
| Sub visible particles | ≥10 μm: ≤6000 p/vial | 3158 | 1020 | 3885 | 905 | 2582 | 4895 | N.R. | 1790 | 888 |
|  | ≥25 μm: ≤600 p/vial | 50 | 5 | 20 | 38 | 47 | 65 | N.R. | 40 | 17 |
| Identification |  |  |  |  |  |  |  |  |  |  |
| Cysteine HCl*$H_2O$ | Same retention time as standard | Complies | Complies | Complies | Complies | Complies | Complies | Complies | Complies | Complies |
| Ibuprofen |  | Complies | Complies | Complies | Complies | Complies | Complies | Complies | Complies | Complies |
| Acetaminophen |  | Complies | Complies | Complies | Complies | Complies | Complies | Complies | Complies | Complies |
| Acetaminophen content (HPLC) | 95-105% | 104 | 104 | 104 | 101 | 99 | 101 | 103 | 104 | 103 |
| Ibuprofen content (HPLC) | 95-105% | 104 | 104 | 103 | 102 | 103 | 100 | 102 | 103 | 103 |
| Cysteine HCl*$H_2O$ (HPLC) | Min 60% | 89% | 86% | 87% | 90% | 87% | 85% | 90% | 72% | 84% |
| Impurities Acetaminophen |  |  |  |  |  |  |  |  |  |  |
| Impurity K (4-aminophenol) | <0.05% | 0.02 | 0.02 | 0.01 | 0.01 | 0.03 | 0.03 | 0.03 | 0.04 | 0.03 |
| Impurity F (4-nitrophenol) | <0.05% | 0.00 | 0.00 | 0.00 | 0.00 | 0.00 | 0.00 | 0.00 | 0.00 | 0.00 |
| Any other impurity | <0.10% | 0.01 | 0.01 | 0.01 | 0.01 | 0.02 | 0.03 | 0.02 | 0.03 | 0.01 |
| Total impurities | <0.2% | 0.0 | 0.0 | 0.0 | 0.0 | 0.0 | 0.1 | 0.0 | 0.1 | 0.0 |
| Impurities Ibuprofen |  |  |  |  |  |  |  |  |  |  |
| Impurity A | <0.1% | 0.0 | 0.0 | 0.0 | 0.0 | 0.0 | 0.0 | 0.00 | 0.00 | 0.00 |
| Impurity B | <0.2% | 0.0 | 0.0 | 0.0 | 0.0 | 0.0 | 0.0 | 0.00 | 0.00 | 0.00 |
| Any other impurity | <0.10% | 0.00 | 0.00 | 0.00 | 0.00 | 0.00 | 0.00 | 0.000 | 0.000 | 0.000 |
| Total impurities | <0.2% | 0.0 | 0.0 | 0.0 | 0.0 | 0.0 | 0.0 | 0.00 | 0.00 | 0.00 |

TABLE 9 storage stability data - 3 mg/ml ibuprofen and 10 mg/ml acetaminophen with cysteine (pH 7.0, 25 +/− 2° C., 40 +/− 5% relative humidity)

| Analysis | Specification | Method and Method No. | 1 month | 2 months | 3 months | 6 months |
|---|---|---|---|---|---|---|
| Appearance of composition | Clear liquid | Visual inspection.USP<641> | clear liquid | clear liquid | clear liquid | clear liquid |
| pH value | To be determined | Potentiometry.USP<791> | 7.02 | 6.99 | 7.00 | 7.00 |
| Coloration | ≤Y 6 | Eur.Ph 2.2.2 | <Y6 | <Y6 | <Y6 | <Y6 |
| Sub visible particles | ≥10 μm: ≤6000 p/vial | Light obscuration particle | 3425 | 2810 | 1142 | 795 |
|  | ≥25 μm: ≤600 p/vial | count method.USP<788> | 37 | 10 | 3 | 5 |
| Deliverable volumes | > 100 ml | Volume measurement.USP<698> | N.R. | N.R. | N.R. | 103 |
| Identification |  |  |  |  |  |  |
| Cysteine HCl*$H_2O$ | Same retention time as standard | Liquid chromatography. | Complies | Complies | Complies | Complies |
| Ibuprofen |  | USP<621> | Complies | Complies | Complies | Complies |
| Acetaminophen |  |  | Complies | Complies | Complies | Complies |
| Acetaminophen content by HPLC | 95-105% | Eur.Ph 2.2.29; 0049 | 97 | 98 | 97 | 95 |
| Ibuprofen content by HPLC | 95-105% | Liquid chromatography. | 99 | 100 | 99 | 97.00 |
| Cysteine HCl*$H_2O$ by HPLC | Min 60% | USP<621> | 75% | 72% | 77% | 83% |
| Acetaminophen |  |  |  |  |  |  |
| Impurity K (4-aminophenol) | <0.05% | Eur.Ph 2.2.29; 0049 | 0.02 | 0.02 | 0.02 | 0.03 |
| Impurity F (4-nitrophenol) | <0.05% |  | 0.00 | 0.00 | 0.00 | 0.00 |
| Any other impurity | <0.10% |  | 0.01 | 0.01 | 0.01 | 0.01 |
| Total impurities | <0.2% |  | 0.2 | 0.2 | 0.1 | 0.2 |

TABLE 9-continued storage stability data - 3 mg/ml ibuprofen and 10 mg/ml acetaminophen
with cysteine (pH 7.0, 25 +/− 2° C., 40 +/− 5% relative humidity)

| Analysis | Specification | Method and Method No. | 1 month | 2 months | 3 months | 6 months |
|---|---|---|---|---|---|---|
| Ibuprofen | | | | | | |
| Impurity A | <0.1% | Eur.Ph 2.2.29 | 0.0 | 0.0 | 0.0 | 0.0 |
| Impurity B | <0.2% | | 0.0 | 0.0 | 0.0 | 0.0 |
| Any other impurity | <0.10% | | 0.00 | 0.00 | 0.00 | 0.00 |
| Total impurities | <0.2% | | 0.0 | 0.0 | 0.0 | 0.0 |

TABLE 10 storage stability test - 3 mg/ml ibuprofen and 10 mg/ml acetaminophen
with cysteine (pH 6.6, 25 +/− 2° C., 40 +/− 5% relative humidity)

| Analysis | Specification | Method and Method No. | 1 month | 2 months | 3 months | 6 months |
|---|---|---|---|---|---|---|
| Appearance of composition | Clear liquid | Visual inspection. USP<641> | Complies | Complies | Complies | Complies |
| pH value | To be determined | Potentiometry. USP<791> | 6.96 | 6.95 | 7.02 | 7.00 |
| Coloration | ≤Y 6 | Eur.Ph 2.2.2 | <Y6 | <Y6 | <Y6 | <Y6 |
| Sub visible particles | ≥10 µm: ≤6000 p/vial | Light obscuration particle | 3250 | 1690 | 2992 | 2407 |
| | ≥25 µm: ≤600 p/vial | count method. USP<788> | 33 | 0 | 3 | 15 |
| Deliverable volumes | >100 ml | Volume measurement. USP<698> | N.R. | N.R. | N.R. | 102 |
| Identification | | | | | | |
| Cysteine HCl*H$_2$0 | Same retention time as standard | Liquid chromatography USP<621> | Complies | Complies | Complies | Complies |
| Ibuprofen | | | Complies | Complies | Complies | Complies |
| Acetaminophen | | | Complies | Complies | Complies | Complies |
| Acetaminophen content by HPLC | 95-105% | Eur.Ph 2.2.29; 0049 | 103 | 103 | 103 | 100 |
| Ibuprofen content by HPLC | 95-105% | Liquid chromatography USP<621> | 104 | 104 | 104 | 102 |
| Cysteine HCl*H$_2$0 by HPLC | Min 60% | | 90 | 85 | 90 | 91 |
| Acetaminophen | | | | | | |
| Impurity K (4-aminophenol) | <0.05% | Eur.Ph 2.2.29; 0049 | 0.02 | 0.02 | 0.02 | 0.02 |
| Impurity F (4-nitrophenol) | <0.05% | | 0.00 | 0.00 | 0.00 | 0.00 |
| Any other impurity | <0.10% | | 0.00 | 0.00 | 0.02 | 0.03 |
| Total impurities | <0.2% | | 0.0 | 0.0 | 0.0 | 0.0 |
| Ibuprofen | | | | | | |
| Impurity A | <0.1% | Eur.Ph 2.2.29 | 0.0 | 0.0 | 0.0 | 0.0 |
| Impurity B | <0.2% | | 0.0 | 0.0 | 0.0 | 0.0 |
| Any other impurity | <0.10% | | 0.00 | 0.00 | 0.00 | 0.00 |
| Total impurities | <0.2% | | 0.0 | 0.0 | 0.0 | 0.0 |

TABLE 11 storage stability test - 3 mg/ml ibuprofen and 10 mg/ml acetaminophen with cysteine (pH 6.4, 25 +/− 2° C., 60 +/− 5% relative humidity)

| Analysis | Specification | Method and Method No. | Release | 1 month | 3 months | 6 months | 9 months | 12 months |
|---|---|---|---|---|---|---|---|---|
| Appearance of composition | Clear liquid | Visual inspection.USP<631>, Ph.Eur.2.2.1 | clear liquid | clear liquid | clear liquid | clear liquid | clear liquid | clear liquid |
| pH | 6.3 - 7.3 | Potentiometry.USP<791> Eur.Ph 2.2.3; Eur.Ph 2.9.17 | 6.4 | 6.6 | 6.8 | 6.9 | 6.9 | 6.9 |
| Coloration | ≤Y 6 | Eur.Ph 2.2.2 | <Y6 | <Y5 | <Y5 | <Y5 | <Y5 | <Y5 |
| Particulate matter | ≥10 µm: ≤6000 p/vial | Light obscuration particle count USP<788> Ph.Eur.2.9.19 | 2331 | 1083 | 229 | 148 | N.R. | 394 |

TABLE 11-continued storage stability test - 3 mg/ml ibuprofen and 10 mg/ml acetaminophen with cysteine (pH 6.4, 25 +/− 2° C., 60 +/− 5% relative humidity)

| Analysis | Specification | Method and Method No. | Release | 1 month | 3 months | 6 months | 9 months | 12 months |
|---|---|---|---|---|---|---|---|---|
|  | ≥25 µm: ≤600 p/vial |  | 43 | 2 | 3 | 2 | N.R. | 2 |
| Identification |  |  |  |  |  |  |  |  |
| Ibuprofen | Same retention time as standard | USP<621> Ph.Eur.2.2.29 | Complies | Complies | Complies | Complies | Complies | Complies |
| Acetaminophen |  |  | Complies | Complies | Complies | Complies | Complies | Complies |
| Cysteine |  |  | Complies | Complies | Complies | Complies | Complies | Complies |
| Acetaminophen content (HPLC) | 95.0-105.0% | Eur.Ph 2.2.29; 0049 | 102.0% | 100.4% | 101.9% | 100.7% | 101.4% | 99.9% |
| Ibuprofen content (HPLC) | 95.0-105.0% | Liquid chromatography USP<621> In house-Ph.Eur.2.2.29 | 98.0% | 99.7% | 99.6% | 98.7% | 98.0% | 10.,2% |
| Cysteine hydrochloride monohydrate (HPLC) | 80-105% at release Min 40% at s.h. | Liquid chromatography USP<621> In house-Ph.Eur.2.2.29 | 84% | 86% | 84% | 78.0% | 77.2% | 80.6% |
| Impurities Acetaminophen |  |  |  |  |  |  |  |  |
| Impurity K (4-aminophenol) | ≤0.05% | Eur.Ph 2.2.29; 0049 | 0.020 | 0.021 | 0.020 | 0.025 | 0.028 | 0.030 |
| Impurity F (4-nitrophenol) | ≤0.05% |  | 0.000 | 0.000 | 0.000 | 0.000 | 0.000 | 0.000 |
| Any other impurity | ≤0.10% |  | 0.017 | 0.013 | 0.019 | 0.010 | 0.017 | 0.011 |
| Total impurities | ≤0.2% |  | 0.037 | 0.035 | 0.039 | 0.035 | 0.045 | 0.041 |
| Impurities Ibuprofen |  |  |  |  |  |  |  |  |
| Impurity A | ≤0.1% | Eur.Ph 2.2.29 | 0.0 | 0.0 | 0.0 | 0.0 | 0.0 | 0.0 |
| Impurity B | ≤0.2% |  | 0.0 | 0.0 | 0.0 | 0.0 | 0.0 | 0.0 |
| Any other impurity | ≤0.10% |  | 0.00 | 0.00 | 0.00 | 0.00 | 0.00 | 0.00 |
| Total impurities | ≤0.2% |  | 0.0 | 0.0 | 0.0 | 0.0 | 0.0 | 0.0 |

The invention claimed is:

1. A method for preparing an intravenously administrable aqueous composition comprising acetaminophen, and optionally one or more non-steroidal anti-inflammatory drugs (NSAIDs), wherein dissolved oxygen of the composition in a closed container is maximally 1.0 ppm, said method comprising
(a) rinsing at least once a compounding vessel with water at a temperature of at least 80° C., wherein each rinsing step comprises introducing a volume of water that is 3-20% of the volume of the compounding vessel and discarding the introduced water thereby heating the vessel to at least 80° C. and creating an oxygen low environment in said vessel by generating a lifting gas in the vessel;
(b) introducing into said compounding vessel one or more excipients;
(c) introducing water for injection at a temperature of 80-99° C., and mixing said introduced excipients and water for injection; and
(d) dissolving acetaminophen in the solution of excipients and water for injection; and
(e) introducing one or more of an isotonic agent, a pH adjusting agent, and anti-oxidant and an NSAID into said compounding vessel after the at least one rinsing step.

2. The method according to claim 1, wherein the water for injection at a temperature of at least 80° C. has a dissolved oxygen content of 0.5 ppm or less.

3. The method according to claim 1, wherein the rinsing of the compounding vessel is with water that is at 90° C. to 99° C. and is repeatedly performed until the compounding vessel has a temperature of at least 90° C.

4. The method according to claim 1, wherein the rinsing of the compounding vessel is repeatedly performed until the oxygen content in the compounding vessel is less than 0.5 ppm.

5. The method according to claim 1, wherein nitrogen pressure is applied by introducing nitrogen gas from an upper side of the vessel.

6. The method according to claim 5, wherein the pH of the composition is adjusted using one or more pH-adjusting agents.

7. The method according to claim 1, wherein nitrogen pressure induces an overpressure of at least 0.1 bar in the compounding vessel.

8. The method according to claim 1, wherein nitrogen pressure induces an overpressure of maximally 1.0 bar in the compounding vessel.

9. The method according to claim 1, wherein approximately 10 mg acetaminophen expressed per ml of said composition is introduced into the compounding vessel subsequent to the one or more rinsing steps.

10. The method according to claim 1, wherein approximately 2 to 4 mg of one or more NSAIDs expressed per ml of said composition is introduced into the compounding vessels subsequent to the one or more rinsing steps.

11. The method according to claim 1, wherein the one or more NSAIDs comprises ibuprofen.

12. The method according to claim 1, wherein the water for injection for the final volume is added to the composition after introducing acetaminophen into the compounding vessel.

13. The method according to claim 1, wherein the one or more anti-oxidants is cysteine or acetyl cysteine.

14. The method according to claim 1, wherein the one or more isotonic agents are selected from the group consisting of mannitol, sorbitol, inositol, glucose and glycerol.

15. The method according to claim 1, wherein the dissolved oxygen content in the composition increases continuously during the method of preparation.

16. The method according to claim 1, wherein the pH of the composition is at 6.3-7.3 prior to introducing acetaminophen.

17. The method according to claim 1, wherein the pH of the composition is adjusted to 6.3-7.3 after introducing acetaminophen.

18. The method according to claim 1, wherein the one or more pH-adjusting agents are selected from the group consisting of hydrochloric acid and sodium hydroxide.

* * * * *